United States Patent [19]

Maybee et al.

[11] Patent Number: 5,338,433
[45] Date of Patent: Aug. 16, 1994

[54] CHROMIUM ALLOY ELECTRODEPOSITION AND SURFACE FIXATION OF CALCIUM PHOSPHATE CERAMICS

[75] Inventors: George W. Maybee, Harvest; Timothy E. Taylor, Huntsville; Elmer L. Field, Huntsville; Clyde Riley, Huntsville; William R. Lacefield, Jr., Birmingham; Harold D. Coble; Harini Dasarathy, both of Huntsville, all of Ala.

[73] Assignee: McDonnell Douglas Corporation, Long Beach, Calif.

[21] Appl. No.: 77,272

[22] Filed: Jun. 17, 1993

[51] Int. Cl.$^5$ .................. C25D 3/56; C25D 13/02
[52] U.S. Cl. ............................ 205/178; 205/176; 205/243; 205/255; 204/181.1; 204/181.5
[58] Field of Search ............ 205/255, 243, 176, 178; 204/181.5, 181.1

[56] References Cited

U.S. PATENT DOCUMENTS

| | | | |
|---|---|---|---|
| 2,377,229 | 5/1945 | Hanford | 205/255 |
| 2,516,227 | 7/1950 | Ma | 205/243 |
| 2,927,066 | 3/1960 | Schaer | 205/243 |
| 3,966,564 | 6/1976 | Hyner et al. | 205/255 |
| 4,196,063 | 4/1980 | Barnes et al. | 205/243 |
| 4,422,920 | 12/1983 | Stachurski et al. | 205/255 |
| 4,610,763 | 9/1986 | Law | 205/243 |
| 4,673,471 | 6/1987 | Kagechika et al. | 205/255 |
| 4,990,163 | 2/1991 | Ducheyne et al. | 427/2 |
| 5,205,921 | 4/1993 | Shirkanzadeh | 204/181.5 |

Primary Examiner—John Niebling
Assistant Examiner—Kishor Mayekar
Attorney, Agent, or Firm—Max Geldin

[57] ABSTRACT

Process for simultaneous electrodeposition of at least a two component alloy system of cobalt and chromium on a substrate, by providing an aqueous solution of divalent cobalt and trivalent chromium ions and containing ethylenediaminetetraacetic acid, at a pH of about 3 to about 5, electrolyzing the solution in an electrolyte cell containing an anode and a cathode, and codepositing cobalt and chromium on the cathode, e.g. titanium, as substrate. According to a preferred embodiment molybdenum-containing ions are also added to the electrolyte, resulting in codeposition of an alloy of cobalt, chromium and molybdenum. In another embodiment, a calcium phosphate ceramic such as hydroxyapatite (HA) is added to the above electrolyte solution, resulting, e.g., in a codeposit of the calcium phosphate material, e.g. HA, and an alloy of cobalt, chromium and molybdenum. In still another embodiment, a calcium phosphate material such as HA, which has been previously attached to a substrate by sintering, is fixated by simultaneous electrodeposition of cobalt-chromium-molybdenum alloy, such codeposits having utility for improvement of medical implants.

24 Claims, No Drawings

CHROMIUM ALLOY ELECTRODEPOSITION AND SURFACE FIXATION OF CALCIUM PHOSPHATE CERAMICS

BACKGROUND OF THE INVENTION

This invention relates to simultaneous electrodeposition of Co-Cr and Co-Cr-Mo alloys onto a base surface during a single electroplating operation. The process accomplishes concurrent deposition of Co and Cr, or Co, Cr and Mo metal atoms, thus creating a homogenous "alloy" surface coating. This electrodeposition process can be applied to fix calcium phosphate ceramics to substrates.

In U.S. application Ser. No. 565,936, filed Aug. 13, 1990, by T. E. Taylor, et al, there is disclosed a process for codeposition of bio-compatible ceramic materials, i.e. calcium phospates and in particular hydroxyapatite (HA), from the same solution during electrodeposition of a metal, such as cobalt, on a suitable substrate or base surface. The objective was to mechanically bond non-metallic bio-compatible ceramic particles to a substrate material by surrounding the particles with electrodeposited metal atoms, thus creating a superiorly bonded composite surface coating containing both metallic and non-metallic materials.

Heretofore, most chromium plating has been, and continues to be, performed using the hexavalent form of chromium as the dichromate ion. Such a process uses an extremely acidic solution which may be detrimental to other materials (i.e., calcium phosphates such as HA) that would be exposed in the plating bath during fixation by the depositing alloy.

Corrosion-resistant chromium-containing alloys, such as cobalt-chromium alloys and particularly cobalt-chromium-molybdenum alloy, a high strength corrosion resistant alloy, have numerous applications. Potential uses for such alloy-plated surfaces are metal structures which are exposed to corrosive environments such as chemical processing equipment. Still another application is prosthetic devices for which this type of alloy is FDA approved—where corrosion resistance and bio-compatibility of a device implanted in living-tissue is of prime importance.

However, as previously noted, not only has the deposition of chromium from electrolytic plating baths required highly acidic solutions, but when attempting to electrolytically plate an alloy containing cobalt and chromium by codeposition thereof, the kinetic rate for cobalt deposition is extremely fast relative to that for chromium, so the resulting electroplated alloy contains only a very small percentage of chromium, and the most desirable alloys of cobalt and chromium, e.g. containing from about 12 to about 33% by weight of chromium, cannot be successfully electrodeposited. Thus, for example, alloys such as Casteloy and Vitallium, containing cobalt, chromium and molybdenum, e.g. used for medical implants, are normally produced by melting, mixing and solidifying these elements in the desired proportions.

It is an object of the present invention to provide a process for electrolytically codepositing at least a two-component system composed of cobalt and chromium.

Another object is the provision of a process of the above type employing a mildly acidic electrolyte solution.

Still another object is to provide a process as noted above using an electrolytic solution under conditions to codeposit at least a two-component system composed of cobalt and a predetermined substantial proportion of chromium.

Yet another object is the provision of a process for electrolytically codepositing a three component system consisting of cobalt, chromium and molybdenum.

Another object is the provision of a process of the above type employing trivalent chromium baths.

A still further object is to provide a process for electrolytically codepositing a three component system consisting of cobalt, chromium and molybdenum, to fix ceramic materials such as a calcium phosphate, e.g. HA, to a substrate surface.

SUMMARY OF THE INVENTION

According to the invention there is provided a process for simultaneous electrodeposition of at least a two component alloy system of cobalt and chromium on a substrate, which comprises providing an aqueous solution of divalent cobalt and trivalent chromium ions and containing ethylenediaminetetraacetic acid (EDTA), at a pH of about 3 to 5, electrolyzing the solution in an electrolytic cell containing an anode and a cathode, and codepositing cobalt and chromium on the cathode substrate, resulting in a homogeneous alloy surface coating.

According to a preferred embodiment molybdenum-containing ions are also added to the electrolyte or electroplating bath, resulting in codeposition of cobalt, chromium and molybdenum.

In another embodiment for producing a ceramic-metal coating on a substrate, a calcium phosphate material such as HA is added to the above electrolyte solution, resulting in strong fixation of the calcium phosphate material by the depositing metallic elements, and resulting, e.g., in a co-deposit of the calcium phosphate material, e.g. HA, and an alloy of cobalt, chromium and molybdenum. Thus, the present invention employing an electrolyte under only mildly acidic conditions permits the incorporation of non-metallic materials such as HA into the electrolyte and then into the alloy co-deposit, without altering or degrading the non-metallic component through exposure to a corrosive environment in the electrolyte or the high temperatures associated with other process methods, such as thermal spraying.

The invention process is unique in that it permits simultaneous electrodeposition of a multi-element metal alloy, particularly a chromium-alloy plated surface coating, in a significantly less corrosive plating solution than is required in standard chromium plating operations. To successfully electroplate cobalt and chromium simultaneously at the desired ratio, a chelating agent, namely EDTA, is required because without it the rate for cobalt deposition is too fast relative to that for chromium. By adding such a chelating agent to the plating bath, the rate of cobalt deposition is reduced such that the desired amount of chromium in the alloy composition can be achieved. To extend the plating capability of this bicomponent system to three components, molybdenum, e.g. in the form of ammonium molybdate, is added to the plating bath.

DETAILED DESCRIPTION OF THE INVENTION AND PREFERRED EMBODIMENTS

In the electrolysis process of the invention, the metal substrate to which the codeposit of cobalt and chromium, or cobalt, chromium and molybdenum is to be applied and which functions as the cathode in the electrolytic cell, can be titanium or an alloy thereof, such as Ti-6Al -4V, stainless steel, e.g. 316 stainless steel, copper, or cobalt-chromium-molybdenum alloy, e.g. Vitallium.

In the electrolytic process of the invention, the anode can be an inert electrode such as carbon, platinum or lead.

The electrolyte solution is in the form of an aqueous solution containing suitable concentrations of the divalent cobalt and trivalent chromium ions for obtaining a two-component codeposit of cobalt and chromium, and also molybdenum-containing ions for obtaining a three-component codeposit of cobalt, chromium and molybdenum. Such ions can be derived from soluble salts of such elements, e.g. the sulfates or chlorides, i.e., cobalt (II) sulfate and chromium (III) sulfate, or cobalt (II) chloride and chromium (III) chloride, and ammonium molybdate.

The concentration of the ions in the electrolyte solution can range from about 0.14 to about 1.4 grams cobalt ions, and from about 11.0 to about 25.0 grams of trivalent chromium ions, per liter of the solution. When molybdenum-containing ions are utilized to codeposit a three-component alloy, the concentration of such ions can range from about 0.13 to about 0.25 grams, per liter of the solution.

Since the rate of deposition of cobalt from the electrolyte solution is fast relative to the rate of deposition of chromium, so that only a minor or very small amount of chromium can be codeposited with the cobalt, it is necessary to slow the cobalt deposition rate in order to increase the relative rate of deposition of the chromium. This is achieved according to the invention by incorporating the chelating agent EDTA into the electrolyte solution. This material chelates with the cobalt ion and reduces the rate of cobalt deposition relative to deposition of chromium. The amount of EDTA or alkali metal salt thereof employed is sufficient to provide a codeposited alloy composition of cobalt and chromium containing up to about 33% chromium, e.g. from about 12 to about 33% chromium, by weight. Using a concentration of EDTA in the solution ranging from about 0.35 to about 3.5 grams per liter of solution, a codeposited two-component alloy of cobalt and chromium can be obtained containing as high as about 33% chromium by weight. The source of ethylenediaminetetraacetic acid can be any compound which produces the acid or its anions in solution, such as, for example, the disodium salt of ethylenediaminetetraacetic acid. By variation of EDTA concentration, an alloy of varying cobalt/chromium ratio may be obtained. For example, a homogeneous codeposited three-component plate alloy containing about 65% Co, 30% Cr and 5% Mo by weight, can be produced from suitable concentrations of $Co^{+2}$ ion, $Cr^{+3}$ ion, molybdate and EDTA.

It has been found that use of other complexing agents such as ethylenediamine and potassium cyanide were essentially ineffective in slowing the rate of deposition of cobalt, and that only small amounts of less than 5%, if any, of chromium codeposited with cobalt under these conditions.

Other auxiliary components can be incorporated into the electrolyte solution. These include ammonium sulfamate and ammonium chloride as buffers, and sodium bromide and potassium bromide, as a source of $Br^-$, which prevents the formation of $Cr^{+6}$. Boric acid can be employed optionally as a brightener. Formic acid can be incorporated as a source of formate anion to provide formation of chromium formate, an electroactive species. These materials can be employed in varying amounts as desired.

As an additional feature of the invention, particularly for the production of medical implants, ceramic material such as a calcium phosphate ceramic can be electrolytically codeposited with the metallic components, e.g. cobalt, chromium and molybdenum, on the substrate. A preferred form of the ceramic material is apatite, a natural calcium phosphate usually containing hydroxide, sometimes with chloride, fluoride or carbonate substituting for part or all of the hydroxide. A particularly preferred apatite is hydroxyapatite, having the formula $Ca_{10}(PO_4)_6(OH)_2$. Another suitable calcium phosphate is tricalcium phosphate, $Ca_3(PO_4)_2$. The terms "ceramic" material and "calcium phosphate" material as employed herein are intended to denote any of the foregoing materials.

The calcium phosphate material in particulate form, e.g. HA, is placed in suspension in an electrolytic medium containing the metallic ions and in which the anode, e.g. platinum, and the metal substrate are suspended, the metal substrate functioning as cathode and spaced appropriately from the anode. The size of the calcium phosphate material particles can range from about 0.1 to about 100 microns, and such particles are maintained in suspension in the electrolyte by suitable stirring.

The concentration of suspended ceramic material, e.g. HA, in the electrolyte bath can range from about 5 to about 60 grams of ceramic material, per liter of electrolyte.

The electrolysis of the electrolyte solution containing the above noted metallic ions, with or without ceramic material, and in the presence of EDTA is carried out using direct current electrodeposition at a voltage sufficient to obtain a current density ranging from about 25 to about 50 $mA/cm^2$. The temperature of the electrolyte bath can be maintained within a temperature range of about 20° to about 50° C., and duration of the electrolysis operation is from about 0.6 to about 600 minutes, e.g. about 300 minutes. The electrolyte bath is maintained under acidic conditions at a pH of about 3 to about 5 by use of potassium hydroxide or sulfuric acid. For example for the codeposition of cobalt and chromium, the pH of the electrolyte is maintained at about 3.5.

An alternative procedure for fixing ceramic to a substrate surface in an alloy consists of first placing the ceramic material (calcium phosphate e.g. hydroxyapatite) in a nonconducting medium, e.g. an alcohol, in an amount of about 25 gms to about 35 gms per liter. With the substrate as cathode and an inert anode, e.g. platinum, and the ceramic suspended by stirring, the ceramic is electrostatically attached by electrophoresis to the substrate by applying a high D.C. voltage to the system for several seconds. The substrate with weakly attached calcium phosphate is removed, air dried and then baked in a furnace. The substrate with attached sintered calcium phosphate ceramic is then placed in the above described electrolyte containing cobalt, chromium and molybdenum-containing ions, and undergoes electrolysis as described to strongly fix the ceramic to the substrate surface with Co-Cr-Mo alloy, but in so doing does not alter the substrate structure, the ceramic structure, or the chemical form of the ceramic.

The codeposition of Co and Cr, or of Co, Cr and Mo, by the foregoing procedures results in a homogeneous alloy plate composition, such as an alloy containing about 67% Co and about 33% Cr, by weight, or an alloy containing about 65% Co, 30% Cr and 5% Mo, by weight, both cobalt alloys containing a substantial proportion of Cr. Where a ceramic material such as HA is incorporated into the surface of the substrate, the HA and the Co-Cr or Co-Cr-Mo alloy, provides a surface coating for high strength medical implants. It has been found that surface coatings prepared in this way are bioactive, well fixed to the surface and the chemical composition of the ceramic material is not altered by the fixation process.

The following are examples of practice of the invention:

EXAMPLE 1

An aqueous electrolyte bath was prepared containing a platinum anode with a metal (copper) substrate serving as cathode. The aqueous bath was composed of 125 g chromium (III) chloride hexahydrate, 1.4 g cobalt (II) chloride hexahydrate, 4.2 g disodium salt of EDTA, 210 g of ammonium sulfamate, 15 g of potassium bromide, 30 g of boric acid, 80 g of ammonium chloride and 60 milliliters of formic acid, per liter of solution. Electrolysis was carried out at an average current density of 30 mA/cm$^2$ at ambient temperature for a period of about 30 minutes.

A codeposited alloy composed of 67% cobalt and 33% chromium, by weight, was obtained on the substrate surface. The plating was homogeneous and free of crazing.

EXAMPLE 2

An aqueous electrolyte bath was prepared containing a platinum anode and a metal Vitallium substrate serving as cathode. The aqueous bath was composed of 125 g chromium (III) chloride hexahydrate, 1.4 g cobalt (II) chloride hexahydrate, 2.8 g ammonium molybdate, 4.2 g disodium salt of EDTA, 210 g of ammonium sulfamate, 15 g of potassium bromide, 30 g boric acid, 80 g ammonium chloride and 60 milliliters of formic acid, per liter of solution.

Electrolysis was carried out at an average current density of 30 mA/cm$^2$ at ambient temperature and for a period of about 30 minutes.

A codeposited alloy was obtained on the substrate surface composed of 66% cobalt, 27% chromium and about 7% molybdenum, by weight, very close to the composition of Vitallium. The plating was homogeneous and free of crazing.

EXAMPLE 3

Using the electrolyte of Example 2, hydroxyapatite of the particle size 10 to 20µm was added in the amount of 40 g per liter. A Vitallium substrate (cathode) with a platinum anode was electrolyzed under the same conditions as Example 2 for a period of 150 minutes. This resulted in a codeposit of alloy and hydroxyapatite with hydroxyapatite covering approximately 38% of the surface area.

EXAMPLE 4

An alternative procedure for fixing ceramic to a substrate surface in an alloy consists of first placing the hydroxyapatite (HA) particles in the nonconducting medium, 2-propanol, in an amount of 30 grams of HA per liter. With Vitallium as a substrate (cathode) and an inert lead anode and the HA suspended by stirring, the HA was electrostatically attached by applying approximately 100 volts D.C. to the system for approximately 60 seconds with the stirrer off. The substrate with attached HA was removed, air dried and then baked in a furnace at 600° C. for approximately 4 hours to sinter the HA and form a modest adhesion of the HA to the Vitallium. The Vitallium with attached sintered HA was then placed in the above described electrolyte of Example 2 and was electrolyzed as described therein to strongly fix the HA to the substrate surface with Co-Cr-Mo alloy, but in so doing did not alter the substrate or HA structure or its chemical form. The HA coverage was 70% of the surface area.

From the foregoing, it is seen that the invention provides a unique process for simultaneous electrodeposition of multiple component alloys, namely Co-Cr alloys and Co-Cr-Mo alloys, employing an electrolytic bath containing Co$^{++}$, Cr$^{+++}$ and which may also include molybdate ions, together with the chelating agent EDTA to permit simultaneous deposition of a substantial amount of chromium together with Co, and which may also include Mo, to form an electroplated alloy surface. The advantages of the present electrolytic process relate to the ability to deposit concurrently several metals in a controlled ratio on a substrate surface, versus one metal at a time, thus achieving a deposited layer of homogeneous alloy metal on the surface. Another feature is the use of weakly acidic electrolyzing solutions which precludes the need for highly acidic and more environmentally hazardous solutions. Yet another feature is the use of the less toxic form of chromium, trivalent versus hexavalent chromium.

Uses for the alloy plated surfaces of the invention include application in corrosive and high wear bearing applications. Codeposition of non-metallic HA with a cobalt-chromium-molybdenum alloy according to the invention provides improved medical implants. In this respect the invention process avoids highly acidic electrolytes which would degrade HA and permits an alloy to be used as a surface coating to "fixate" or mechanically retain non-metallic HA particles without changing their original chemical composition.

Since various changes and modifications of the invention will occur to those skilled in the art within the spirit of the invention, the invention is not to be taken as limited except by the scope of the appended claims.

What is claimed is:

1. A process for simultaneous electrodeposition of at least a two component alloy system of cobalt and chromium on a substrate which comprises electrolyzing an aqueous solution consisting essentially of divalent cobalt and trivalent chromium ions and ethylenediaminetetraacetic acid, at a pH of about 3 to about 5, in an electrolytic cell containing an anode and a cathode, and codepositing cobalt and chromium on said cathode as the substrate.

2. A process for simultaneous electrodeposition of at least a two component alloy system of cobalt and chromium on a substrate which comprises electrolyzing an aqueous solution consisting essentially of divalent cobalt, trivalent chromium ions and ethylenediaminetetraacetic acid, at a pH of about 3 to about 5, using an anode selected from the group consisting of carbon, platinum and lead, and a cathode selected from the group consisting of titanium and alloys thereof, stainless steel, copper and cobalt-chromium-molybdenum alloy, and codepositing cobalt and chromium on said cathode as the substrate.

3. The process of claim 1, including employing an amount of said ethylenediaminetetraacetic acid sufficient to provide said codeposited alloy of cobalt and chromium containing up to about 33% chromium by weight.

4. The process of claim 1, including adding molybdenum-containing ions to said solution, and said codepositing comprising codepositing cobalt, chromium and molybdenum on said cathode as the substrate.

5. The process of claim 4, including employing an amount of said ethylenediaminetetraacetic acid sufficient to provide a codeposited alloy of cobalt, chromium and molybdenum, containing about 12 to about 33% chromium by weight.

6. The process of claim 5, the amount of cobalt, chromium and molybdenum containing ions in said solution being sufficient to provide a codeposited alloy consisting of about 65% cobalt, about 30% chromium and about 5% molybdenum, by weight.

7. The process of claim 1, said electrolyzing taking place at a current density of about 25 to about 50 mA/cm$^2$.

8. The process of claim 1, said cobalt and trivalent chromium ions being provided by soluble chromium (III) and soluble cobalt (II) salts.

9. The process of claim 4, said cobalt, trivalent chromium and molybdenum ions being provided by soluble chromium (III), soluble cobalt (II) and soluble molybdate salts.

10. The process of claim 9, said salts being chromium chloride, cobalt chloride and ammonium molybdate.

11. The process of claim 1, employing about 0.14 to about 1.4 grams cobalt (II) ions, about 11.0 to about 25.0 grams trivalent chromium ions, and about 0.35 to about 3.5 grams ethylenediaminetetraacetic acid, per liter of said solution.

12. The process of claim 4, employing about 0.14 to about 1.4 grams cobalt (II) ions, about 11.0 to about 25.0 grams trivalent chromium ions, about 0.13 to about 0.25 grams molybdenum-containing ions, and about 0.35 to about 3.5 grams ethylenediaminetetraacetic acid, per liter of said solution.

13. The process of claim 4, and including adding a calcium phosphate ceramic to said solution and said codepositing comprising codepositing said calcium phosphate and an alloy of said cobalt, chromium and molybdenum on said cathode as the substrate.

14. The process of claim 13, wherein said calcium phosphate ceramic is hydroxyapatite.

15. The process of claim 12, and including adding to said solution about 5 to about 60 grams of hydroxyapatite, per liter of said solution, and said codepositing comprising codepositing said hydroxylapatite and an alloy of said cobalt, chromium and molybdenum on said cathode as the substrate.

16. The process of claim 12, including initially fixing calcium phosphate ceramic to said cathode substrate by electrophoresis and sintering.

17. The process of claim 16, said electrophoresis including placing calcium phosphate ceramic particles in a nonconducting medium containing an inert anode and said substrate as cathode in an amount of about 25 gms to about 35 gms per liter, and applying about 100 volts for about 60 seconds to weakly attach said calcium phosphate ceramic to said substrate, said sintering comprising heat treating said substrate with weakly attached calcium phosphate ceramic at about 600° C. for about 4 hours to hold the calcium phosphate ceramic to the substrate.

18. The process of claim 16, said calcium phosphate ceramic being hydroxyapatite.

19. The process of claim 17, said calcium phosphate ceramic being hydroxyapatite.

20. An electrolyte solution for simultaneous electrodeposition of at least a two component alloy system of cobalt and chromium on a substrate consisting essentially of about 0.14 to about 1.4 grams cobalt (II) ions, about 11.0 to about 25.0 grams trivalent chromium ions, and about 0.35 to about 3.5 grams ethylenediaminetetraacetic acid, per liter of said solution.

21. The electrolyte solution of claim 20, said electrolyte solution also containing about 0.13 to about 0.25 grams molybdenum-containing ions per liter of said solution, capable of forming a codeposited alloy of cobalt, chromium and molybdenum, containing about 12 to about 33% chromium by weight on said substrate.

22. The electrolyte solution of claim 21, said electrolyte solution also containing about 5 to about 60 grams of hydroxyapatite per liter of said solution, capable of forming a codeposit of hydroxyapatite and an alloy of said cobalt, chromium and molybdenum on said substrate.

23. The process of claim 1, including adding formic acid to said solution.

24. The process of claim 12, including adding 60 ml of formic acid and 15 grams of potassium bromide per liter of solution, to said solution.

* * * * *